(12) United States Patent
Kubick et al.

(10) Patent No.: US 9,951,366 B2
(45) Date of Patent: Apr. 24, 2018

(54) CELL-FREE PROTEIN SYNTHESIS METHOD AND DEVICE USING A EUKARYOTIC CELL LYSATE IN THE PRESENCE OF A CASPASE INHIBITOR AND THE USE OF A CASPASE INHIBITOR FOR INCREASING THE YIELD AND/OR THE STABILITY OF THE SYNTHESIZED PROTEINS IN SUCH A METHOD

(71) Applicant: Fraunhofer-Gesellschaft zur Foerderung der angewandten Forschung e. V., Munich (DE)

(72) Inventors: Stefan Kubick, Berlin (DE); Marlitt Stech, Potsdam (DE); Doreen Wuestenhagen, Potsdam (DE); Robert Quast, Berlin (DE)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 0 days.

(21) Appl. No.: 15/024,125

(22) PCT Filed: Sep. 17, 2014

(86) PCT No.: PCT/EP2014/002520
§ 371 (c)(1),
(2) Date: Mar. 23, 2016

(87) PCT Pub. No.: WO2015/043729
PCT Pub. Date: Apr. 2, 2015

(65) Prior Publication Data
US 2016/0251692 A1 Sep. 1, 2016

(30) Foreign Application Priority Data

Sep. 25, 2013 (DE) .................. 10 2013 015 977
Dec. 11, 2013 (DE) .................. 10 2013 020 900

(51) Int. Cl.
| | |
|---|---|
| *C12P 21/00* | (2006.01) |
| *C12P 21/02* | (2006.01) |
| *C07K 5/08* | (2006.01) |
| *C07K 5/10* | (2006.01) |
| *C07K 5/083* | (2006.01) |
| *C07K 5/113* | (2006.01) |
| *C07K 5/107* | (2006.01) |
| *C12M 1/00* | (2006.01) |

(52) U.S. Cl.
CPC ............ *C12P 21/00* (2013.01); *C07K 5/0808* (2013.01); *C07K 5/1016* (2013.01); *C07K 5/1021* (2013.01); *C12M 23/34* (2013.01); *C12M 29/04* (2013.01); *C12P 21/02* (2013.01)

(58) Field of Classification Search
None
See application file for complete search history.

(56) References Cited

U.S. PATENT DOCUMENTS

2002/0106631 A1* 8/2002 Alnemri ............... C12N 9/6475
435/4
2006/0024781 A1 2/2006 Garvin et al.

FOREIGN PATENT DOCUMENTS

WO 9935277 A2 7/1999

OTHER PUBLICATIONS

Callus et al., "Caspase inhibitors: viral, cellular and chemical", Cell Death Differ. 14(1): pp. 73-78 (2007).
Carlson et al., "Cell-free protein synthesis: applications come of age", Biotechnol Adv. 30(5): pp. 1185-1194 (2012).
Ekert et al., "Caspase inhibitors", Cell Death Differ. 6(11): pp. 1081-1086 (1999).
Hofweber, "Analyse kritischer Einflussfaktoren auf die Proteinexpression im zellfreien System", Thesis of the University of Regensburg (PhD) (2007).
English language abstract of Hofweber, "Analyse kritischer Einflussfaktoren auf die Proteinexpression im zellfreien System", Thesis of the University of Regensburg (PhD) (2007).
Katzen et al., "The past, present and future of cell-free protein synthesis", Trends Biotechnol. 23(3): pp. 150-156 (2005).
Madin et al., "A highly efficient and robust cell-free protein synthesis system prepared from wheat embryos: plants apparently contain a suicide system directed at ribosomes", Proc Natl Acad Sci U S A. 97(2): pp. 559-564 (2000).
Merk et al., "Cell-free synthesis of functional and endotoxin-free antibody Fab fragments by translocation into microsomes", Biotechniques. 53(3): pp. 153-160 (2012).
Spirin et al., "A continuous cell-free translation system capable of producing polypeptides in high yield", Science 242(4882): pp. 1162-1164 (1988).
Thermo Scientific, "Instructions: Pierce Human In Vitro Protein Expression Kit for DNA Templates", Pierce Biotechnology, pp. 1-6 (2010).
International Search Report for PCT/EP2014/002520 dated Apr. 7, 2015.

* cited by examiner

*Primary Examiner* — Addison D Ault
(74) *Attorney, Agent, or Firm* — Caesar Rivise, PC

(57) ABSTRACT

The invention relates to an improved cell-free protein synthesis method using a eukaryotic cell lysate in the presence of a caspase inhibitor, to a device for carrying out said method, and to the use of a caspase inhibitor for increasing the protein yield or for increasing the stability of the synthesized proteins in such a cell-free protein synthesis method using a eukaryotic cell lysate. In a preferred embodiment of the invention, the cell-free protein synthesis method is carried out as a continuous method in a device which comprises at least two compartments separated by a dialysis membrane. The translation reaction takes place in at least one first compartment, the reaction compartment, and during the translation reaction i) reactants are diffused from at least one other compartment, the supply and discharge compartment, into the reaction compartment, and ii) reaction byproducts are diffused from the reaction compartment into the supply and discharge compartment by means of the dialysis membrane. According to the invention, the caspase inhibitor is provided at least in the reaction compartment but can also be preferably provided in the supply and discharge compartment in order to supply unused inhibitors to the reaction compartment.

10 Claims, 10 Drawing Sheets

CELL-FREE PROTEIN SYNTHESIS METHOD AND DEVICE USING A EUKARYOTIC CELL LYSATE IN THE PRESENCE OF A CASPASE INHIBITOR AND THE USE OF A CASPASE INHIBITOR FOR INCREASING THE YIELD AND/OR THE STABILITY OF THE SYNTHESIZED PROTEINS IN SUCH A METHOD

SEQUENCE LISTING STATEMENT

Incorporated herein by reference in its entirety is a Sequence Listing named "B118020282_SequenceListing_ST25", which is being submitted to the USPTO via EFS-web on even date herewith as an ASCII text file 6 KB in size. This file, which was created on Mar. 22, 2016, constitutes both the paper and computer readable form of the Sequence Listing.

The invention relates to an improved method for cell-free protein synthesis using a eukaryotic cell lysate in the presence of a caspase inhibitor, a device for carrying out this method and the use of a caspase inhibitor for increasing the protein yield and/or for increasing the stability of the synthesized proteins in such a cell-free method for protein synthesis using a eukaryotic cell lysate.

BACKGROUND OF THE INVENTION

In the relatively recent past, cell-free protein synthesis has become established as an efficient alternative to the expression of proteins in vivo (Carlson, E. D. et al., Biotechnology Advances, 2012, 30(5): pp. 1185-1194). Herein, the contents of the cell are used in order to manufacture a particular target protein in a rapid, reliable and cost-effective manner. The cell extracts obtained, also referred to as cell lysates, contain the essential components that are needed for the cell-free synthesis of proteins: ribosomes, translation factors and enzymes. Nowadays, selected recombinant proteins can be manufactured in a functionally active form in prokaryotic as well as in eukaryotic cell lysates. The following translation systems based on eukaryotic cell lysates are increasingly used currently: wheatgerm lysates, reticulocyte lysate, insect cell lysates and cell extracts from HeLa and HeLa hybridoma cells.

Compared with prokaryotic in vitro translation systems based on *Escherichia coli*, the protein yields achieved using most of the eukaryotic translation systems are relatively low (Carlson et al., above). An exception in this regard is the extremely efficient wheatgerm lysate expression system. Depending on the protein and reaction format, this achieves several hundred micrograms of protein per milliliter of reaction volume (Madin, K. et al., Proc. Natl. Acad. Sci. USA, 2000. 97(2): pp. 559-64). However, this cell extract is not suitable for synthesizing proteins with posttranslational modifications like, for example, glycosylations.

Eukaryotic translation systems based on insect cell lysates and reticulocyte lysates enable the synthesis of complex structured eukaryotic proteins with posttranslational modifications which cannot be synthesized in *Escherichia coli*. However, reticulocyte lysates must be enriched for this purpose with microsomal membranes of another species (heterogeneous translation system) In contrast thereto, cell lysates from *Spodoptera frugiperda* can be used as a homogeneous translation system, since the cell lysate and the membrane vesicles contained are obtained from the same cell line. By means of suitable cell decomposition methods, eukaryotic cell lysates can be obtained which contain components of an important cellular compartment, specifically the endoplasmic reticulum. All proteins that are discharged from the cell or are incorporated into the cell membrane, carry sugar residues or have disulphide bridges for stabilizing their molecular structure, migrate through this cellular compartment. Cell lysates which contain structures of the ER, so-called microsomes or membrane vesicles, can now be used to manufacture such protein candidates in a functionally active form. In this way, incompatibilities between the vesicles and the cytosolic proteins of the lysate are prevented, with the consequence of relatively high protein yields (up to 20 µg/ml in insect cell lysates in batch mode) and an efficient transport of target proteins into the microsomes of the lysate.

Cell-free protein synthesis reactions can be realized experimentally in a variety of ways. The simplest reaction route is the synthesis of a target protein in a one-pot synthesis (or batch reaction). Batch-based systems are therefore suitable for uncomplicated and rapid synthesis of a target protein. On the other hand, however, they are characterized by short run times and relatively low protein yields.

In general, a batch-based cell-free translation reaction reaches the maximum of synthesized target protein after 1-1.5 hours. Incubation times beyond this do not lead to increased protein yields, but result, with a high probability, in a reduction of the concentration of target protein, possibly due to the proteolytic decomposition of the target proteins, for example, by proteases present in the cell extract. However, it would be highly advantageous in particular cases also to preserve the synthesized target proteins over longer incubation times (>2 h) in an intact form in the translation solution.

One possibility for prolonging the run time of a cell-free protein synthesis reaction in order thereby to obtain greater protein yields is the use of dialysis systems (continuous exchange cell-free systems, CECF; Spirin, A. et al., Science, 1988, 242(4882): pp. 1162-4). Herein, energy-rich substances such as ATP and GTP pass by diffusion through a membrane into the reaction compartment, the site of the translation. At the same time, the reaction is depleted of inhibiting substances such as free phosphates and ADP.

The continuous supply of the cell-free reaction in the reaction compartment prolongs the run time of the synthesis and leads to significantly raised protein yields as compared with the batch system. Dialysis systems of this type are already commercially available, although exclusively in combination with prokaryotic cell lysates from *Escherichia coli* or with wheatgerm lysates.

Despite the yield increase as compared with discontinuous batch systems, the protein yield with corresponding eukaryotic dialysis systems is still relatively low compared with an *Escherichia coli*-based system.

Against this background, it is an object of the invention to provide means for enabling the synthesis of complex eukaryotic and prokaryotic proteins in a stable and functionally active form, particularly membrane proteins or proteins with posttranslational modifications in a relatively large quantity in a cell-free translation system.

This object is solved according to the invention by the method for cell-free protein synthesis according to the invention, wherein a eukaryotic cell lysate is used and the translation reaction is carried out in the presence of a caspase inhibitor, the use of a caspase inhibitor according to the invention, and the device for carrying out a method of the invention.

DESCRIPTION OF THE INVENTION

A main aspect of the present invention relates to a method for cell-free protein synthesis which comprises an in vitro translation reaction using a nucleic acid template and a eukaryotic cell lysate, characterized in that the translation reaction is carried out in the presence of a caspase inhibitor.

The eukaryotic cell lysate used is not specifically restricted and principally comprises any cell lysate which contains all the components required for in vitro translation of the nucleic acid template. Particularly preferred is a cell lysate which also enables the synthesis of complex proteins with posttranslational modifications.

In a more specific embodiment, the eukaryotic cell lysate used is selected from the group comprising wheatgerm lysates, insect cell lysates, in particular Sf21 cell lysates, reticulocyte lysates, keratinocyte lysates, cell extracts from CHO cells, HeLa cells, hybridoma cells or cultivated lymphoma cells.

These cell lysates can be used in their native form or modified by addition or removal of particular components.

If the cell lysate obtained primarily from one cell line contains, for example, no membrane vesicles (e.g. reticulocyte lysates), these can be added from another source, for example, the lysate of another cell line, in order also to enable the synthesis of proteins with posttranslational modifications. Furthermore, the presence of the membranous vesicles in the lysate is the precondition for the embedding of membrane proteins in a native lipid-protein-matrix, which ensures its correct folding and conformation.

Conversely, it can be advantageous, for the synthesis of particular proteins, to use a cell lysate which naturally contains no membrane vesicles or which has been freed from vesicles, for example, by means of a centrifuging step. The use of this "vesicle-depleted" cell lysate can lead, for particular proteins, to an increase in yield (see example 1, FIG. 1).

The "vesicle-depleted" cell lysate is also translation-active and can be used for cell-free synthesis of proteins without posttranslational modifications.

The components of the cell lysate used can thus originate from cells of a cell line (homogeneous translation system) or from different cell lines (heterogeneous translation system). The use of artificial cell lysates in which one or more components have been synthetically produced is also possible in principle.

The reaction mixture for carrying out the method according to the invention contains, apart from the eukaryotic cell lysate and the caspase inhibitor, at least one nucleic acid template, a polymerase, amino acids and energy-rich substances such as ATP, GTP, etc. In principle, all the reaction mixtures and components which are known for in vitro translation systems can be used (after addition of the caspase inhibitor). The reaction mixture can possibly also contain further additives which promote the synthesis or stability of particular target proteins, for example, DTT or other reducing agents, particularly mixtures of reduced and oxidized glutathione.

As shown by the experiments described and the test data below, the addition of a caspase inhibitor to a cell-free eukaryotic translation system, particularly using continuous dialysis systems, surprisingly enables a significant increase in the protein yield, as has been shown also for complex proteins with posttranslational modifications.

The biochemical mechanism for this effect of a caspase inhibitor on the synthesis performance of the cell-free protein synthesis reaction is currently still unclear. During the cell disruption, the cells are subjected to great stress which possibly induces apoptotic processes. The apoptosis is also referred to as "programmed cell death" which is substantially controlled by an enzyme class with proteolytic activity, the "caspases". It is suspected that the inhibition of the caspases by the caspase inhibitor prolongs the lifespan of particular translation factors in the lysate which, in turn, could have a positive effect on the overall synthesis output of the cell extract.

A further advantage of the presence of a caspase inhibitor in a cell-free protein synthesis system using a eukaryotic cell lysate resides in a positive influence on the stability of the synthesized proteins, particularly under conditions in which these proteins remain longer (e.g. >1.5 h) in the translation mixture. This concerns, for example, reactions in which the cell-free synthesis of one or more target proteins takes place in a plurality of successive syntheses in the same microsome mixture. This type of reaction route is known as "multiple or repetitive synthesis" and serves to enrich de novo synthesized target proteins in the lumen or the membrane of microsomal vesicles.

In principle any irreversible or reversible inhibitor of a caspase, in particular one of the currently known caspase types 1-14, is suitable as a caspase inhibitor. Caspase inhibitors are described, for example, in the following publications: Callus, B. A. and D. L. Vaux, *Caspase inhibitors: viral, cellular and chemical*. Cell Death Differ, 2006. 14(1): pp. 73-78; Ekert, P. G., Silke, J., Vaux, D. L., Caspase inhibitors. Cell Death Differ, 1999, 6: pp. 1081-1086.

A specific embodiment of the method according to the invention is characterized in that the caspase inhibitor is an amino acid derivative or a peptide derivative comprising an amino acid or peptide sequence which serves as a substrate for a caspase, in particular one or more of the caspase types 1-14, and a functional group which irreversibly or reversibly binds to a caspase, in particular one or more of the caspase types 1-14. The caspase inhibitor is herein a competitive inhibitor.

More specifically, the method is characterized in that the caspase inhibitor comprises the amino acid aspartate or a peptide sequence which contains the amino acid aspartate. Caspases cleave peptide bonds C-terminal of aspartate (D). The amino acid aspartate is therefore contained in each commercial peptide-based caspase inhibitor.

Still more specifically, the amino acid or peptide sequence is selected from the group containing aspartate, valine-alanine-aspartate (VAD), aspartate-glutamate-valine-aspartate (DEVD; SEQ ID NO:1) and tyrosine-valine-alanine-aspartate (YVAD; SEQ ID NO:2). An inhibitor with the sequence VAD is preferred since this is a general caspase inhibitor.

However, inhibitors with another peptide, for example, Ac-DEVD-CMK (SEQ ID NO:1; inhibits caspase 3, 6, 7, 8, 10), Z-WEHD-FMK (SEQ ID NO:3; caspase 1), Z-AEVD-FMK (SEQ ID NO:4; caspase 10), Z-LEED-FMK (SEQ ID NO:5; caspase 13), Z-VDVAD-FMK (SEQ ID NO:6; caspase 2), Z-DEVD-FMK (SEQ ID NO:1; caspase 3), Z-YVAD-FMK (SEQ ID NO:2; caspase 4), Z-VEID-FMK (SEQ ID NO:7; caspase 6), Z-IETD-FMK (SEQ ID NO:8; caspase 8), Z-LEHD-FMK (SEQ ID NO:9; caspase 9) are also usable.

The functional group can, in principle, be any group which reversibly or irreversibly binds to the active center of a caspase and blocks its activity. Various such groups are already known for other enzymes and a person skilled in the art can easily identify suitable representatives of these groups with routine inhibition experiments.

The functional group of the inhibitor defines its mechanism of action. Peptides which are coupled to the functional group methylketone (e.g. fluoromethylketone (FMK), chloromethyl-ketone (CMK), acylmethylketone and (phosphinyloxy)-methylketone)) act as irreversible inhibitors (e.g. Z-VAD-FMK, Ac-VAD-CMK, Ac-DEVD-CMK (SEQ ID NO:1)). Peptides which are coupled to aldehydes (or nitriles and ketones) act as reversible inhibitors (e.g. Ac-AAVALL-PAVLLALLAPDEVD-CHO (SEQ ID NO:10) or other reversible inhibitors with the amino acid aspartate or the sequence DEVD (SEQ ID NO:1) or VAD).

In a specific embodiment of the invention, the caspase inhibitor comprises the functional groups fluoromethylketone (FMK), chloromethylketone (CMK) or difluorophenoxy-methylketone, which bind irreversibly to all caspase types 1-14.

In another specific embodiment of the invention, the caspase inhibitor is a peptide which is coupled to at least one aldehyde group and which reversibly inhibits a caspase (e.g. Ac-AAVALLPAVLLALLAPDEVD-CHO (SEQ ID NO:10)). The peptide preferably has one of the above sequences.

The concentration of the caspase inhibitor can vary greatly depending on the type of cell lysate used and the type and mode of action of the inhibitor used. However, the optimum concentration can easily be determined by a person skilled in the art through routine experiments.

Typically, the caspase inhibitor is present in a concentration of 20 μM to 100 μM, preferably 25 to 50 μM, for example approximately 30 μM, in the reaction mixture.

In a particularly preferred embodiment, the method according to the invention is continuously carried out in a per se known dialysis system.

Typically, the method is carried out in a device which comprises at least two compartments separated by a dialysis membrane, wherein the translation reaction takes place in at least one first compartment, the reaction compartment, and, during the translation reaction, i) reactants diffuse through the dialysis membrane out of at least one further compartment, the supply and discharge compartment, into the reaction compartment and ii) reaction by-products diffuse through the dialysis membrane out of the reaction compartment into the supply and discharge compartment.

The caspase inhibitor is herein present at least in the reaction compartment, although it can preferably also be present in the supply and discharge compartment in order to supply further fresh inhibitor to the reaction compartment.

The presence of the caspase inhibitor in the reaction mixture enables substantially longer run times for the reaction (for example, up to 48 h or even longer) and thereby leads to significant protein yield increases.

With a continuous process of this type, on use of a caspase inhibitor according to the invention, including for complex proteins with posttranslational modifications, a maximum protein yield of at least 30 μg/ml of reaction medium, preferably at least 100 μg/ml or 150 μg/ml, can be achieved.

A closely related aspect of the present invention therefore relates to the use of a caspase inhibitor to increase the protein yield in a cell-free continuous process for protein synthesis using a eukaryotic cell lysate.

Preferably, this caspase inhibitor is an inhibitor as defined above.

In more concrete terms, this use is characterized in that the maximum protein yield measured in μg/ml of reaction medium is increased by a factor or at least 2, particularly at least 5 or 10, as compared with an analogue system in the absence of the caspase inhibitor. Herein, protein yields of at least 30 μg/ml of reaction medium, preferably at least 100 μg/ml or 150 μg/ml, are achieved, even for complex proteins with posttranslational modifications.

A further related aspect of the present invention relates to the use of a caspase inhibitor to increase the stability of the synthesized proteins in a cell-free method for protein synthesis using a eukaryotic cell lysate, particularly under conditions in which these proteins remain a relatively long time (e.g. >1.5 h) in the translation mixture.

Preferably, this caspase inhibitor is an inhibitor as defined above and particularly preferably an irreversible inhibitor as defined above.

In a specific embodiment, this use is characterized in that the cell-free method for protein synthesis comprises at least the following steps:

a) sintering the target protein by means of an in vitro translation reaction in a reaction medium comprising a nucleic acid template which encodes for the target protein, a cell lysate which contains membrane vesicles and a caspase inhibitor;

b) separating membrane vesicles which contain the synthesized target protein from the medium;

c) transferring the separated membrane vesicles into a secondary reaction medium, comprising a nucleic acid template which codes for the target protein, a cell lysate which contains no membrane vesicles and a caspase inhibitor, executing an in vitro translation reaction in the presence of the caspase inhibitor in the secondary reaction medium, and separating membrane vesicles which contain an increased quantity of the synthesized target protein from the secondary medium, wherein step c) can be repeated once or a plurality of times.

A further aspect of the present invention relates to a device for carrying out the method according to the invention for cell-free protein synthesis.

Typically, the device according to the invention for carrying out a cell-free protein synthesis comprises at least two different separate compartments:

at least one reaction compartment in which an in vitro translation reaction takes place and which contains the reaction mixture which comprises at least one eukaryotic cell lysate, a polymerase, a nucleic acid template, amino acids and energy-rich substances such as ATP, GPT, etc.;

at least one supply and discharge compartment which is separated by a semipermeable dialysis membrane from the reaction compartment and contains amino acids, energy-rich substances and reaction by-products;

and is characterized in that at least the reaction compartment, preferably also the supply and discharge compartment, contains a caspase inhibitor as defined above.

The proteins synthesized with the method according to the invention can be either prokaryotic or eukaryotic proteins.

Particularly preferably, they are membrane proteins or complex proteins with posttranslational modifications. Such modifications can be, for example, disulphide bridges, glycosylations, lipid modifications and other known modifications.

The translation system described here making use of a eukaryotic cell lysate and the addition of the caspase inhibitor represents a significant advance in the field of recombinant protein expression. Both preparative and analytical uses of the proteins manufactured are made significantly simpler and more efficient by the yield increases and stability improvements achieved. This is of great interest particularly in the domain of the expression of membrane proteins in order to clarify protein structures.

EXAMPLE 1

Influence of the Caspase Inhibitor on the Expression of a Cytosolic Protein in a Cell-Free Translation System Making Use of a Eukaryotic Cell Extract from *Spodoptera frugiperda*

The influence of the caspase inhibitor on the maximum achievable protein yield was initially investigated on the basis of the expression of the cytosolic protein SII-eYFP. This model protein is the enhanced yellow fluorescent protein (eYFP) which was fused at the N-terminus with an affinity tag (Strep-Tag, SII-Tag) and was present in the vector pIX3.0 (Qiagen).

The expression of the model protein was analyzed in the batch system and the dialysis system (50 µl reaction chamber; 1000 µl feeding chamber; cut-off of the membrane=10 kDa) over a period of 48 h. The translation mixtures were each incubated in the batch system and the dialysis system with (+) and without (−) insect cell vesicles (V) and with (+) and without (−) caspase inhibitor (CI) (at 27° C. and 600 rpm). The protein synthesis was carried out in the presence of the radioactively labeled amino acid $^{14}$C-leucine in order to be able to determine the quantity of de novo synthesized target protein by means of hot TCA precipitation and scintillation measurement.

The translation reactions were interrupted at particular time points (0 h, 2 h, 4 h, 24 h and 48 h) and analyzed as follows: 5 µl of the mixture was precipitated in hot TCA or ice-cold acetone in each case. A further 5 µl was resuspended in 25 µl PBS. The remaining sample volume was separated by means of a centrifuging step into the supernatant fluid (SN) and the vesicular fraction (VF). Aliquots of 5 µl of these fractions were diluted in 25 µl PBS each.

Following the TCA precipitation, the samples were separated from free radioactive amino acids via a vacuum-driven filtration system and underwent a scintillation measurement.

After drying, the proteins precipitated in acetone were collected in a reducing sample buffer and separated electrophoretically.

The samples resuspended in PBS were examined in the phosphorimager system (Typhoon TRIO+ imager, GE Healthcare) for their fluorescence intensity. For this purpose, 25 μl samples were pipetted into each cavity of the Ibidi slides and measured, the excitation of the samples taking place at 488 nm and the emission being measured at 526 nm.

Figure 1:
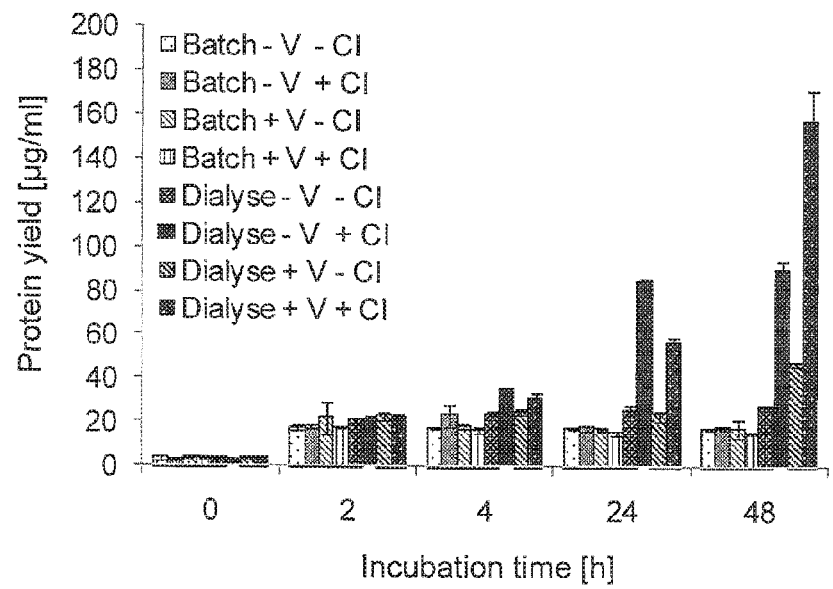
FIG. 1 shows the influence of the caspase inhibitor (CI) Z-VAD-FMK (benzyloxycarbonyl-Val-Ala-Asp-[O-methyl]-fluoromethylketone) on the synthesis of the cytosolic protein SII-eYFP in a cell-free eukaryotic translation system on the basis of a cell extract from *Spodqptera frugiperda* (Sf21) insect cells.
A: Graphical representation of the protein yield of SII-eYFP established by $^{14}$C-leucine incorporation.
B: Autoradiograph to illustrate $^{14}$C-leucine-labelled SII-eYFP. The protein shows an apparent molecular mass of approximately 29 kDa.
C: Analysis of the fluorescence intensity of the cell-free synthesized protein SII-eYFP.
D: Graphical representation of the fluorescence intensities obtained under C. TM=total translation mixture. SN=supernatant fluid after centrifuging. VF=vesicular fraction. V=vesicles.
Figure 1:
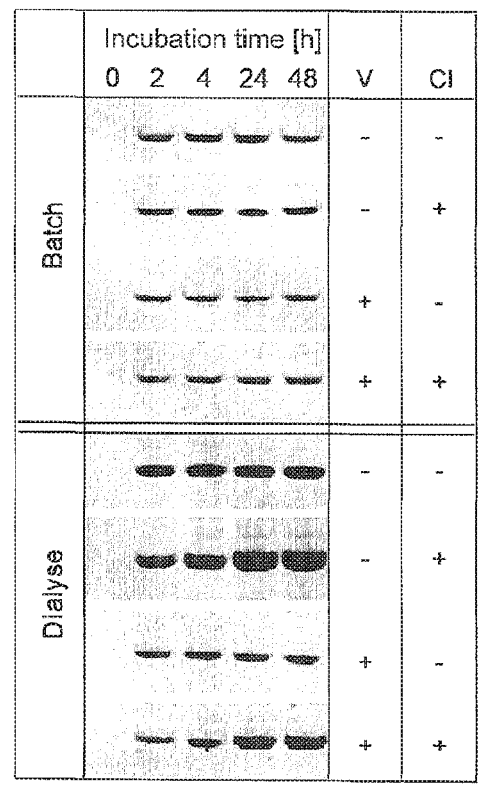
Figures 1C, 1D:
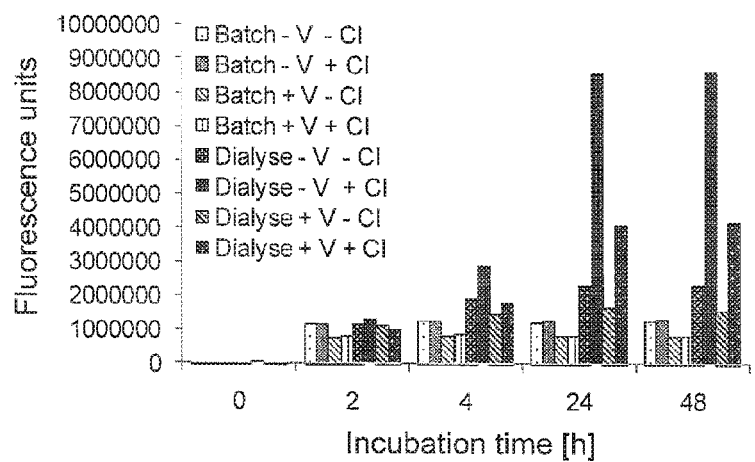

The results shown in FIG. 1 illustrate that without the addition of the caspase inhibitor, a moderate increase in the protein quantity (approximately 50%) was achieved in the dialysis system as compared with the batch system (batch system after 48 h, −V, −CI=17.5 μg/ml; dialysis system after 48 h, −V, −CI=27.1 μg/ml). In contrast thereto, the addition of the caspase inhibitor to the translation mixture led to a very large increase (approximately 400%) of the maximum protein yield achieved of 17.3 μg/ml (batch system after 48 h, −V, +CI) to 90.8 μg/ml of target protein (dialysis system after 48 h, —V, +CI) (FIG. 1A). The fluorescence recordings of the samples showed a similar tendency. The fluorescence signal detected from the translation mixtures that were synthesized in the dialysis system in the presence of the caspase inhibitor significantly differed from the other samples (FIG. 1C). The densitometric evaluation of these samples reveals a 3.7 times more intense fluorescence signal of the samples expressed in the dialysis system −CI (after 48 h, −V) as compared with the dialysis system +CI (after 48 h, −V) (FIG. 1D).

EXAMPLE 2

Influence of the Caspase Inhibitor on the Expression of Membrane Proteins in a Cell-Free Translation System Making Use of a Eukaryotic Cell Extract from *Spodoptera frugiperda*

Here, the influence of the caspase inhibitor on the expression of different membrane proteins in the eukaryotic translation system was investigated more closely. For this purpose, three different model proteins were selected: the endothelin-B receptor (ETB) is a G-protein coupled receptor with seven transmembrane domains which was used cloned into the vector pIX3.0 (Qiagen) for the expression. Furthermore, the type I transmembrane protein heparin-binding EGF-like growth factor (Hb-EGF), N-terminally fused to the melittin signal sequence and C-terminally fused to eYFP, present in the vector pIX3.0, was used for the expression. In addition, the expression of the membrane protein bacteriorhodopsin which also has seven transmembrane domains and was present in the vector pMA (GeneArt) was investigated.

Figure 2:
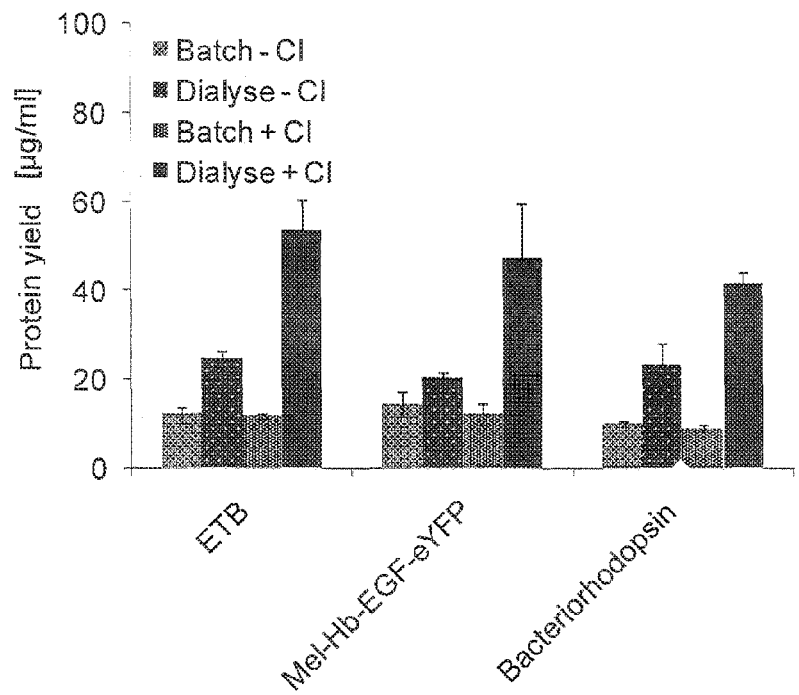
FIG. 2 shows the influence of the caspase inhibitor (CI) Z-VAD-FMK on the expression of membrane proteins in a cell-free eukaryotic translation system on the basis of a cell extract from *Spodoptera frugiperda* (Sf21) insect cells.
A: Graphical representation of the protein yields obtained in the batch and dialysis systems.
B: Autoradiograph of the proteins synthesized in the batch system (B) and the dialysis system (D). Control=translation mixture without the addition of a DNA template.
Figure 2:
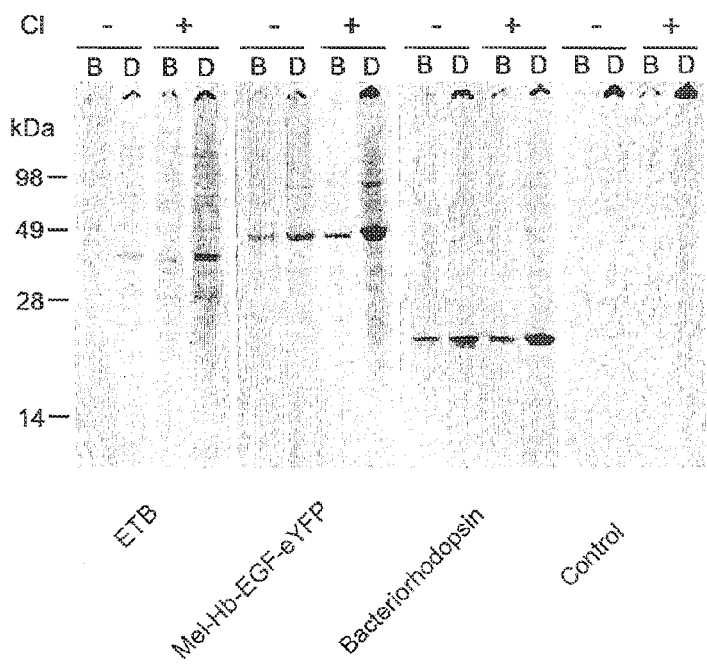

The three proteins were each expressed in the batch and dialysis systems without (−) and with (+) the addition of the caspase inhibitor (CI) in the presence of $^{14}$C-leucine for 48 h (27° C.; 600 rpm, Eppendorf Thermomixer Comfort) and analyzed as in example 1. The determination of the protein yields achieved by means of scintillation measurement shows a clear influence of the caspase inhibitor on the maximum achievable protein yields. The expression of each of the three membrane proteins (ETB, 49.3 kDa; Hb-EGF, 51 kDa; bacteriorhodopsin, 26.9 kDa) was able to be increased in the dialysis system (comparison of the dialysis batches +CI and −CI) with the addition of the caspase inhibitor by approximately 100% (FIG. 2).

EXAMPLE 3

Influence of the Reducing Agent Dithiothreitol (DTT) on the Maximum Achievable Protein Yields Using a Eukaryotic Cell Extract and the Addition of the Caspase Inhibitor The addition of reducing agents such as DTT to cell extracts and translation buffers conventionally served to prolong the shelf life. However, investigations on the cell-free expression of proteins with disulphide bridges have revealed that reducing agents can inhibit formation of disulphide bridges in the target protein (Katzen, F., G. Chang and W. Kudlicki, Trends Biotechnol., 2005, 23(3): pp. 150-156). Since disulphide bridges represent important post-translational modifications in many proteins, which give the protein stability and make an important contribution to protein folding, a variety of experiments have been undertaken to develop translation systems with a defined redox potential. For this purpose, in most cases, the addition of reducing agents to the lysate or the translation buffer is omitted.

The cell-free translation system described here is intended to offer a platform with which complex eukaryotic proteins can be synthesized. It was therefore of particular interest to determine whether the method according to the invention can also be used advantageously for the synthesis of proteins with disulphide bridges and to reveal optimization possibilities.

For this purpose, the influence of the reducing agent DTT on the synthesis performance of the batch and dialysis system with different model proteins was investigated.

The synthesis of the glycoprotein erythropoietin (N-terminally fused to a melittin signal sequence; Mel-EPO; 20.9 kDa, unglycosylated) and of ETB (49.3 kDa), luciferase (60.6 kDa), Mel-Hb-EGF-eYFP (51 kDa) and bacteriorhodopsin (26.9 kDa) was carried out in the batch (B) and dialysis system (D) with the addition of the caspase inhibitor (Z-VAD-FMK) without (−) and with (+) the addition of DTT in the translation buffer in the presence of $^{14}$C-leucine for 48 h, 27° C. and 600 rpm.

Figure 3:
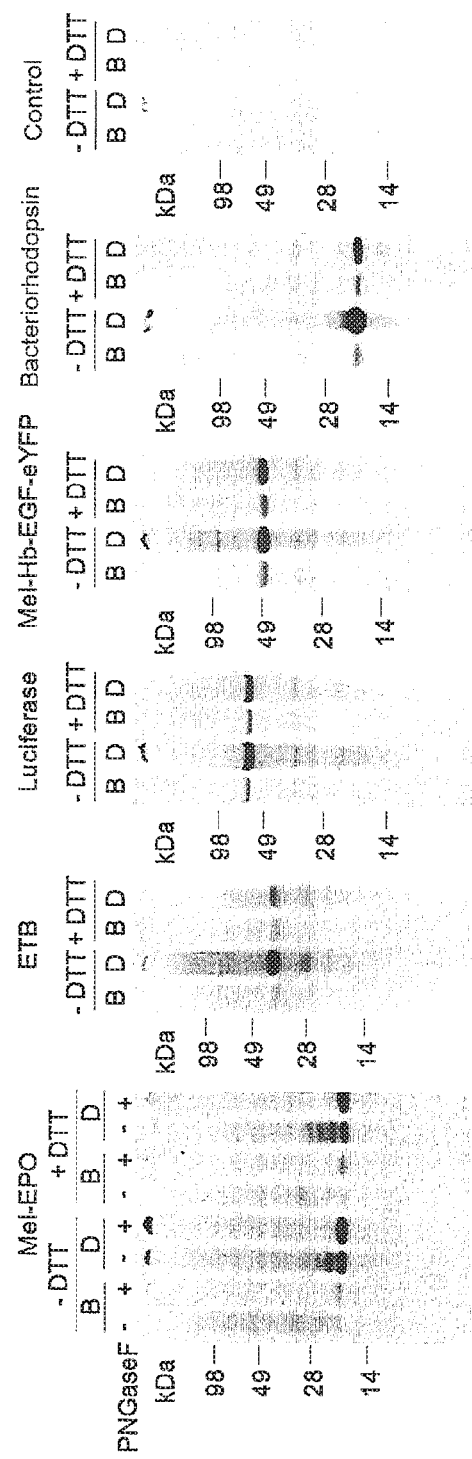
FIG. 3 shows the influence of the reducing agent dithiothreitol (DTT) on the expression of different model proteins in the cell-free eukaryotic translation system on the basis of a cell extract from *Spodoptera frugiperda* (Sf21) insect cells. The figure shows the autoradiograph of the proteins synthesized in the batch system and the dialysis system. Control=translation mixture without the addition of a DNA template.

FIG. 3 shows the autoradiograph of the proteins synthesized in the batch system and the dialysis system. Control=translation mixture without the addition of a DNA template.

It is apparent that the absence of DTT has no negative effect on the expression of different model proteins, including cytosolic proteins (luciferase, SII-eYFP; both present in the expression vector pIX3.0, Qiagen) and membrane proteins (ETB, Mel-Hb-EGF-eYFP, bacteriorhodopsin).

In the case of the glycosylated protein erythropoietin (N-terminally fused to a melittin signal sequence; Mel-EPO), it was however found that complete glycosylation of the target protein could only be achieved in the presence of DTT.

EXAMPLE 4

Investigation of the Expression of the Type-I Transmembrane Protein Mel-Hb-EGF-eYFP Using a Eukaryotic Cell Extract and the Addition of a Caspase Inhibitor It is apparent from the above data that the addition of the caspase inhibitor to the protein synthesis reaction can increase the maximum achievable yields of membrane protein in the dialysis system by an average of approximately 100%. For the transmembrane protein Mel-Hb-EGF-eYFP, an increase in the total protein quantity from 20.5 µg/ml (dialysis 48 h −CI) to 47.6 µg/ml (dialysis 48 h+CI) was achieved (=130%). On a comparison of the batch system with the dialysis system, an increase in the total protein quantity from 12.1 µg/ml (batch 48 h+CI) to 47.6 µg/ml (dialysis 48 h+CI) was achieved (=300%) (FIG. 2).

Figure 4:
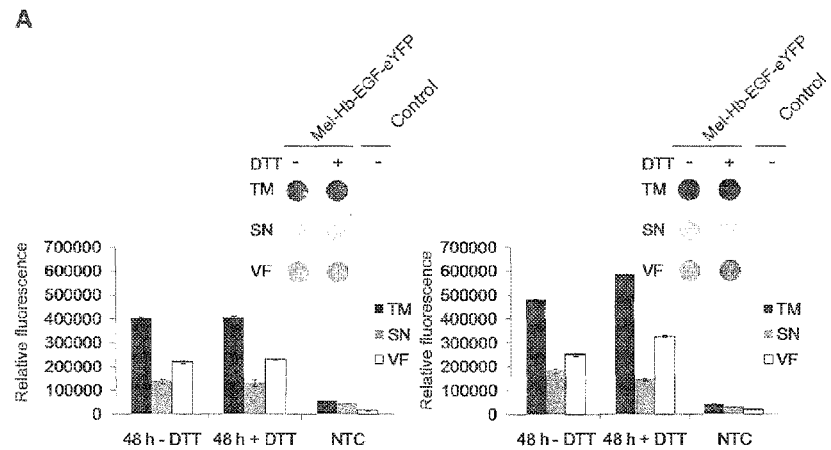
FIG. 4 shows the expression of the type-I transmembrane protein Mel-Hb-EGF-eYFP in the cell-free eukaryotic translation system on the basis of a cell extract from *Spodoptera frugiperda* (Sf21) insect cells.
A: Synthesis of Mel-Hb-EGF-eYFP in the batch (left) and dialysis system (right) in the absence (−) and in the presence (+) of DTT with the addition of the caspase inhibitor Z-VAD-FMK.
B: Graphical representation of the protein yields of Mel-Hb-EGF-eYFP established by $^{14}$C-leucine incorporation in the translation mixture (TM) and the vesicular fraction (VF) over a period of 48 h in the batch system (left) and the dialysis system (right).
C: Autoradiograph to reveal $^{14}$C-leucine-labelled Mel-Hb-EGF-eYFP. The protein shows an apparent molecular mass of approximately 51 kDa.
Control=translation mixture without the addition of a DNA template.
Figure 4:
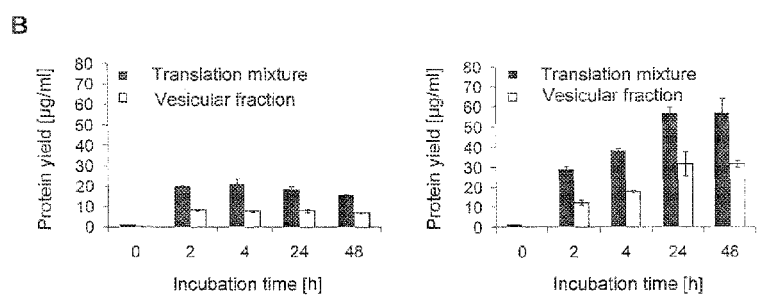
Figure 4:
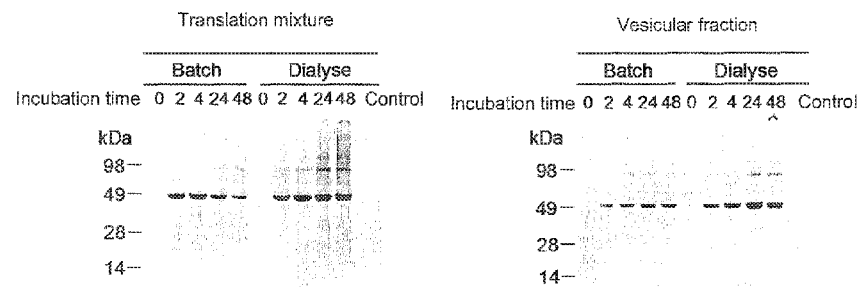

Here, the intention was to investigate whether the increase in the total protein quantity is also associated with an increase in the quantity of membrane protein translocated and integrated into the lipid layer of the vesicles. For this purpose, the translation mixtures of Mel-Hg-EGF-eYFP were separated by means of a centrifuging step into the supernatant fluid (SN) and the vesicular fraction (VF). Aliquots (5 µl) of these samples were used for determining the quantity of de novo synthesized protein or were investigated with regard to their fluorescence properties (FIG. 4).

FIG. 4A: The synthesis of Mel-Hb-EGF-eYFP was carried out in the batch (left) and dialysis system (right) in the absence (−) and in the presence (+) of DTT with the addition of the caspase inhibitor (Z-VAD-FMK) over 48 h at 27° C. and 600 rpm. Following the synthesis, the mixtures were separated by means of a centrifuging step into the supernatant fluid (SN) and the vesicular fraction (VF). For analysis of the fluorescence intensity of the samples, aliquots of the fractions (5 µl) were each diluted in 25 µl PBS and 25 µl of this mixture was pipetted to each cavity of the Ibidi slide and measured. Excitation of the samples was carried out at 488 nm with a phosphorimager (Typhoon TRIO+ Imager, GE Healthcare) and the emission measured at 526 nm.

FIG. 4B shows a graphical representation of the protein yields of Mel-Hb-EGF-eYFP, established by means of the incorporation of $^{14}$C-leucine, in the translation mixture (TM) and the vesicular fraction (VF) over a period of 48 h analyzed in the batch system (left) and the dialysis system (right).

FIG. 4C shows an autoradiograph to reveal $^{14}$C-leucine-labelled Mel-Hb-EGF-eYFP. The protein has an apparent molecular mass of approximately 51 kDa.

These data show that the use of the dialysis system with the inclusion of the caspase inhibitor and in the absence of DTT leads to a significant increase in the proportion of Mel-Hb-EGF-eYFP in the vesicular fraction of the lysate (batch 48 h −DTT+CI=6.5 µg/ml; dialysis 48 h −DTT+CI=31.4 µg/ml). Furthermore, the time-dependent analysis of samples of the vesicular fraction in the dialysis system shows a continuous increase in the protein quantity over 24 h, whereas in the batch system, the maximum is reached after 2 h (FIGS. 4B, 4C).

EXAMPLE 5

The Influence of Irreversible and Reversible Caspase Inhibitors on the Synthesis Performance in the Eukaryotic Translation System on the Basis of a Cell Extract from *Spodoptera frugiperda* (Sf21) Insect Cells Using the example of the fluorescent protein SII-eYFP, the influence of different irreversible caspase inhibitors (Z-VAD-FMK, Ac-VAD-CMK, Ac-DEVD-CMK (SEQ ID NO:1), Q-VD-OPh) and of a reversible caspase inhibitor (Ac-AAVALLPAVLLALLAPDEVD-CHO (SEQ ID NO:10)) on the synthesis was investigated in a eukaryotic dialysis translation system.

The translation of SII-eYFP was carried out using the DNA template pIX3.0-SII-eYFP over 48 h at 600 rpm and 27° C. in the batch and dialysis modes in the presence of different irreversible and reversible caspase inhibitors. All inhibitors were used in a concentration of 30 µM. Following the completion of translation, the different mixtures were examined in the phosphorimager system (Typhoon TRIO+ imager, GE Healthcare) for their fluorescence intensity. For this purpose, 5 µl of each translation mixture was resuspended in 25 µl PBS. Subsequently, 25 µl of this sample was pipetted into a cavity of an Ibidi slide and measured, the excitation of the samples taking place at 488 nm and the emission being measured at 526 nm.

Figure 5:
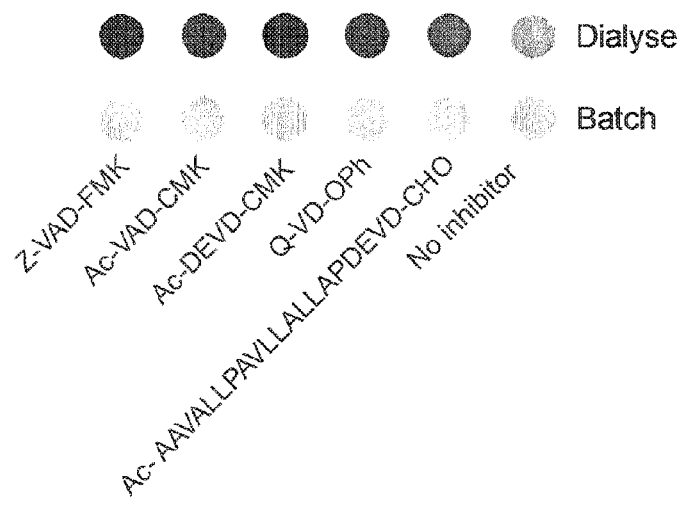
FIG. 5 shows the influence of irreversible caspase inhibitors (Z-VAD-FMK, Ac-VAD-CMK, Ac-DEVD-CMK (SEQ ID NO:1), Q-VD-OPh) and of a reversible caspase inhibitor (Ac-AAVALLPAVLLALLAPDEVD-CHO (SEQ ID NO:10)) on the synthesis of the fluorescent protein SII-eYFP in a eukaryotic translation system on the basis of a cell extract from *Spodoptera frugiperda* (Sf21) insect cells.
Ac-VAD-CMK=acetyl-Val-Ala-Asp-chloromethylketone.
Ac-DEVD-CMK=acetyl-Asp-Glu-Val-Asp-chloromethylketone (SEQ ID NO:1). Q-VD-OPh=N-(2-quinolyl)-Val-Asp-(2,6-difluorophenoxy)-methylketone. Ac-AAVALL-PAVLLALLAPDEVD-CHO=acetyl-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO:10).
A: Representation of the relative fluorescence intensities of all samples in the batch mode and the dialysis mode.
B: Graphical evaluation of the relative fluorescence intensity of SII-eYFP in the batch mode and the dialysis mode. The fluorescence intensities of the samples were normalized and the fluorescence intensity of the dialysis mixture without the addition of a caspase inhibitor represents 100%.
Figure 5:
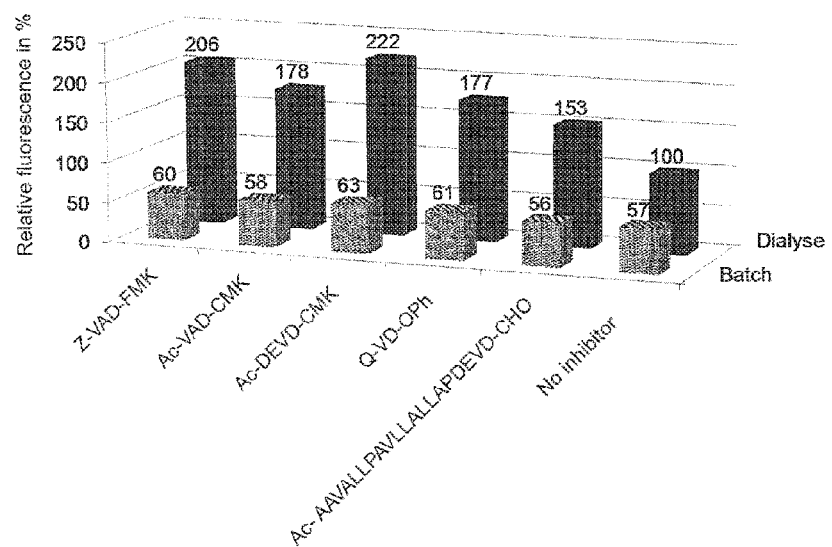

The results presented in FIG. 5 show that all the tested irreversible caspase inhibitors were able to increase the synthesis yield by at least 77% (Q-VD-OPh) up to a maximum of 122% (Ac-DEVD-CMK; SEQ ID NO:1) as compared with a control dialysis mixture without inhibitor. The reversible caspase inhibitor Ac-AAVALLPAVLLALLAP-DEVD-CHO (SEQ ID NO:10) tested caused an increase in the yield of fluorescing protein by 53% as compared with the dialysis solution without inhibitor.

On the basis of the data described, it can therefore be concluded that in principle with both irreversible and reversible inhibitors, an increase in the synthesis yield is possible in the eukaryotic dialysis system.

EXAMPLE 6

Influence of the Caspase Inhibitor Z-VAD-FMK on the Stability of a De Novo Synthesized Membrane Protein in the Eukaryotic Translation System The positive influence of the caspase inhibitor on the stability of cell-free synthesized proteins is shown here on the basis of the expression of the EGF receptor, the protein being a human, high molecular weight transmembrane protein (Epidermal Growth Factor Receptor) with intrinsic tyrosine kinase activity. The coding sequence of the EGF receptor was fused N-terminally with a melittin signal sequence (Mel) and C-terminally with yellow fluorescent protein (eYFP) and cloned into the vector pIX3.0 (Qiagen). The model protein is denoted below as Mel-hEGFR-eYFP (=163 kDa). The melittin signal sequence enables translocation of the membrane protein into the microsomes of the eukaryotic cell extract and subsequently embedding into the membrane of the microsomes. Mel-hEGFR-eYFP has nine potential N-glycosylation sites and therefore, due to the translocation of the target protein, N-glycosylation of the target protein is also enabled in the cell-free system.

Figure 6:
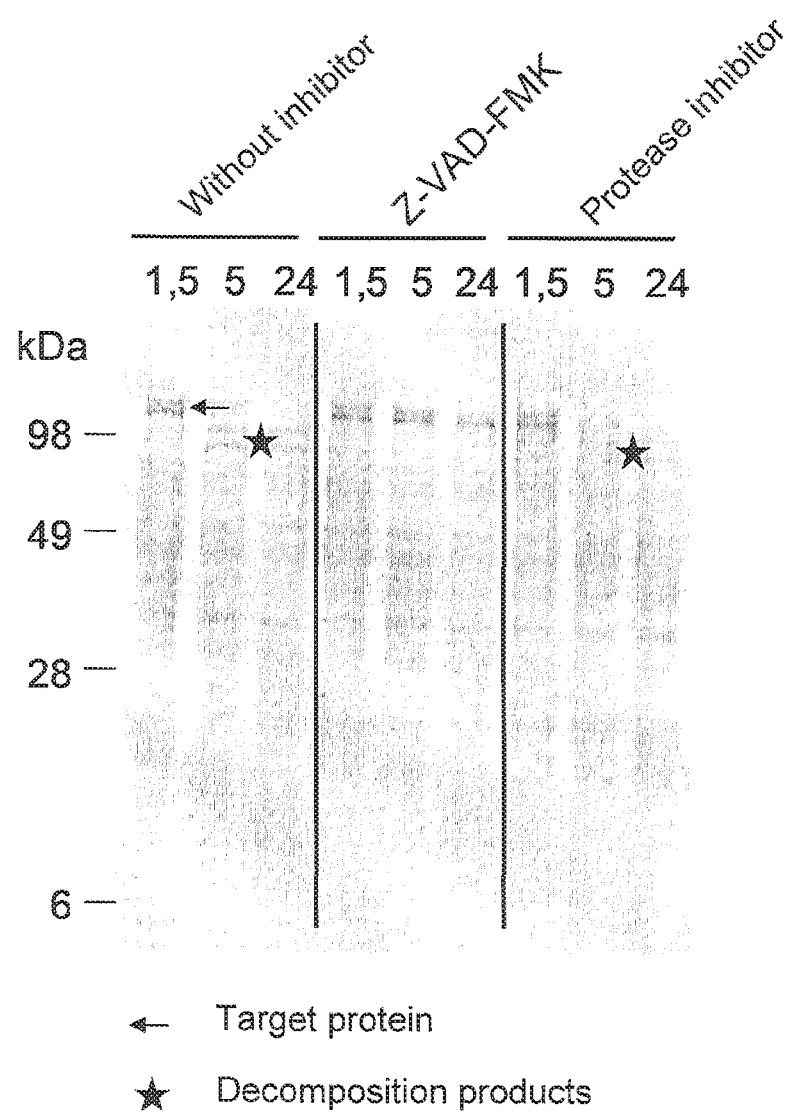
FIG. 6 shows the influence of the caspase inhibitor Z-VAD-FMK on the stability of the de novo synthesized membrane protein Mel-hEGFR-eYFP in a cell-free eukaryotic translation system based on Sf21 insect cell lysates in batch mode.

FIG. 6 shows the cell-free expression of Mel-hEGFR-eYFP in a batch-based eukaryotic translation system based on Sf21 insect cell lysates in the presence of $^{14}$C-leucine. The translation reaction was carried out in the absence and the presence of a caspase inhibitor (Z-VAD-FMK, Promega, 30 µM) and a protease inhibitor mixture ("Complete Protease Inhibitor Cocktail", Roche), respectively, and stopped at the indicated incubation times (1.5 h, 5 h and 24 h) by freezing the translation reaction in liquid nitrogen. The analysis of the de novo synthesized target proteins was carried out using SDS-PAGE and autoradiography. For the execution of the SDS-PAGE, 5 µl of the translation mixture were precipitated in ice-cold acetone. Following drying, the protein pellets were collected in reducing sample buffer and separated in a 10% SDS-PAGE. The visualization of the cell-free synthesized and $^{14}$C-leucine-labelled proteins was carried out using the phosphorimager system (Typhoon TRIO+ imager, GE Healthcare).

The autoradiograph shows two distinct bands of the target protein after 1.5 h incubation time. Due to the numerous potential N-glycosylation sites in the sequence of the target protein, it is suspected that the band with the larger molecular weight is the protein with one or more added N-glycosylations. The protein band with the lower molecular weight would therefore correspond to the target protein without sugar groups. Without the addition of the caspase inhibitor, it can be seen for Mel-hEGFR-eYFP after just 5 h incubation time that the band intensity of the target protein in the autoradiograph decreases and lower-molecular decomposition products become visible. In contrast thereto, the proteins which have been synthesized in the presence of the caspase inhibitor show reduced signs of a proteolytic decomposition. Even after 24 h incubation time the membrane protein Mel-hEGFR-eYFP is detectable in an intact form in the autoradiograph. The specific effect of the caspase inhibitor is therefore made clear, in that the addition of a commercially available protease inhibitor mixture (Complete Protease Inhibitor Cocktail, Roche) did not achieve the stabilizing effect of the caspase inhibitor.

EXAMPLE 7

Positive Influence of Different Caspase Inhibitor Types on the Stability of a De Novo Synthesized Membrane Protein in the Eukaryotic Translation System In the following experiment, the effect of different caspase inhibitors (Z-VAD-FMK, Promega; Ac-DEVD-CMK (SEQ ID NO:1), SantaCruz Biotechnology; Q-VD-OPh, Z-WEHD-FMK (SEQ ID NO:3), Z-VDVAD-FMK (SEQ ID NO:6), Z-DEVD-FMK (SEQ ID NO:1), Z-YVAD-FMK (SEQ ID NO:2), R&D Systems; all 30 µM) with different functional groups (methylketone, fluoromethylketone, FMK or chloromethylketone, CMK) and peptide groups on the synthesis of the target protein Mel-hEGFR-eYFP in a cell-free eukaryotic translation system based on Sf21 insect cell lysates in batch mode in the presence of $^{14}$C-leucine was investigated. The synthesis was stopped at the incubation times given in FIG. 7 (1.5 h; 24 h).

Figure 7:
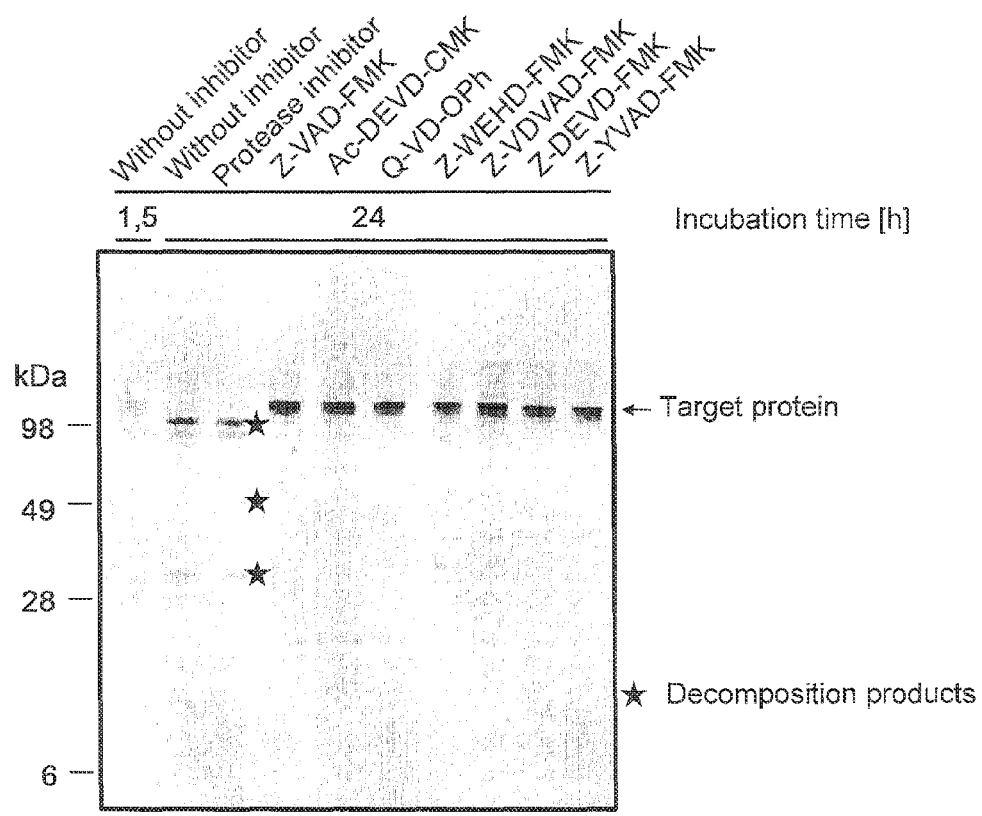
FIG. 7 shows the influence of different caspase inhibitors (Z-VAD-FMK; Ac-DEVD-CMK (SEQ ID NO:1); Q-VD-OPh, Z-WEHD-FMK (SEQ ID NO:3), Z-VDVAD-FMK (SEQ ID NO:6), Z-DEVD-FMK (SEQ ID NO:1), Z-YVAD-FMK (SEQ ID NO:2)) on the stability of the de novo synthesized membrane protein Mel-hEGFR-eYFP in a cell-free eukaryotic translation system based on Sf21 insect cell lysates in batch mode.

The results obtained show that all the inhibitors used ensure the stability of the target protein in the translation solution, even after long incubation times (24 h) (FIG. 7).

EXAMPLE 8

Figure 8:
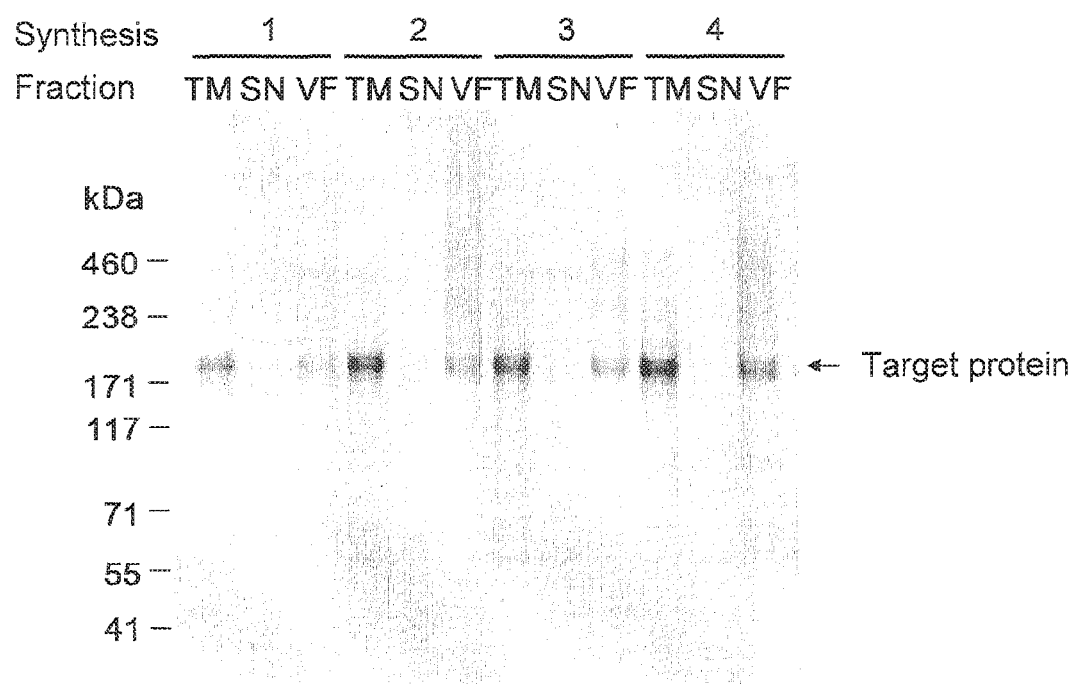
FIG. 8 shows repetitive syntheses of the membrane protein Mel-hEGFR-eYFP into the microsomes of the insect cell lysate in the presence of the caspase inhibitor Z-VAD-FMK. The following examples serve to describe the invention in greater detail but without limiting the same to the specific boundary conditions and parameters of these examples.
Figure 8:
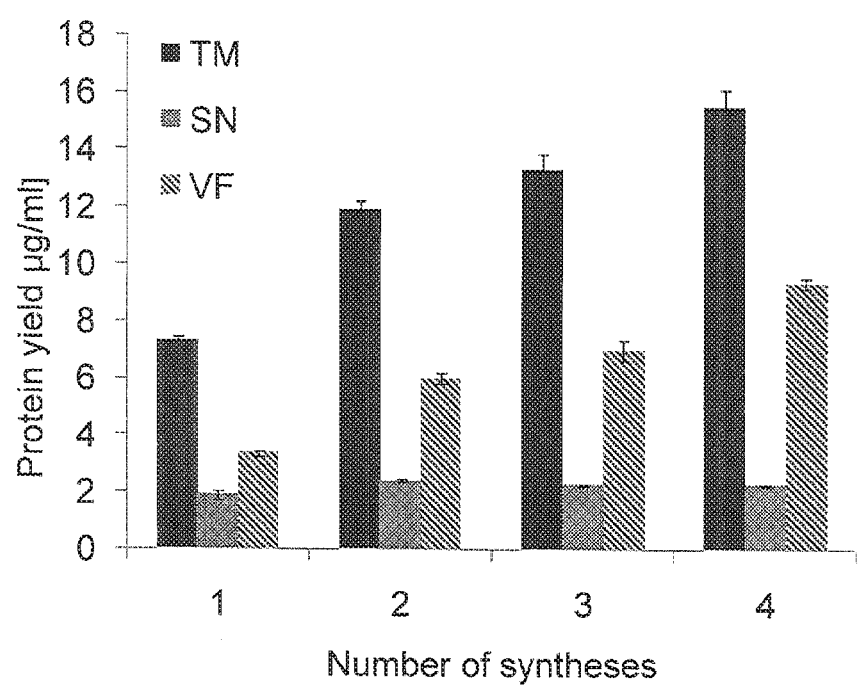

Use of the Caspase Inhibitor Z-VAD-FMK with Multiple Synthesis of a Target Protein in Microsomal Vesicles A suitable method for increasing the concentration of a particular target protein in the lumen or the membrane of the insect cell vesicles lies in carrying out multiple syntheses. This procedure leads to a longer dwell time of the de novo synthesized target proteins in the translation mixture. For successful conversion, it is therefore absolutely necessary to ensure the stability of the target proteins even after relatively long incubation times (>1.5 h) in the translation mixture. For this purpose, the caspase inhibitor Z-VAD-FMK was added to the translation reaction. The multiple synthesis of the target protein was carried out as follows: the microsomes of the translation mixture incubated under standard conditions (27° C., 1.5 h) were pelleted with a centrifugation step at 16,000 g and resuspended in a new translation-active cell lysate without microsomes and incubated again for 1.5 h at 27° C. in the presence of the caspase inhibitor Z-VAD-FMK. In the present experimental example, the synthesis was repeated four times. Following each synthesis step, the yield of radioactively labeled protein in the translation mixture, the supernatant and the vesicular fraction were determined. In addition, 5 µl of the translation mix were precipitated in acetone and subsequently separated out electrophoretically. The associated autoradiograph (FIG. 8A) shows the protein bands of Mel-hEGFR-eYFP in the translation mixture and the vesicular fraction of the translation mixture. The addition of the caspase inhibitor to the translation reaction enables a synthesis of the target protein over a total of 6 h.

The data obtained show that the yield of target protein was increased from synthesis steps 1 to 4 by 110% (total protein in the translation mixture) and by 180% (vesicular fraction) respectively.

The invention claimed is:

1. A method for cell-free protein synthesis, said method comprising:
   providing a device which comprises a reaction compartment, a supply and discharge compartment and a dialysis membrane separating the reaction compartment from the supply and discharge compartment, and
   carrying out an in vitro translation reaction using a nucleic acid template and a eukaryotic cell lysate,
   wherein: (a) the eukaryotic cell lysate is selected from the group consisting of insect cell lysates, cell extracts from CHO cells, HeLa cells, hybridoma cells and cultivated lymphoma cells, (b) the translation reaction takes place in the reaction compartment, and during the translation reaction, i) reactants diffuse through the dialysis membrane out of the supply and discharge compartment, into the reaction compartment and ii) reaction byproducts diffuse through the dialysis membrane out of the reaction compartment into the supply and discharge compartment, and (c) the translation reaction is carried out in the presence of a caspase inhibitor in the reaction compartment.

2. The method according to claim 1, wherein the caspase inhibitor is an amino acid derivative or a peptide derivative comprising an amino acid or peptide sequence which serves as a substrate for a caspase, and a functional group which irreversibly or reversibly binds to a caspase.

3. The method according to claim 2, wherein the caspase inhibitor is a derivative of the amino acid aspartate or is the peptide derivative wherein the peptide sequence comprises the amino acid aspartate.

4. The method according to claim 3, wherein the amino acid or peptide sequence of the peptide derivative is selected from the group consisting of aspartate, valine-alanine-aspartate (VAD), aspartate-glutamate-valine-aspartate (DEVD; SEQ ID NO: 1) and tyrosine-valine-alanine-aspartate (YVAD; SEQ ID NO:2).

5. The method according to claim 1, wherein the caspase inhibitor comprises, as a functional group, a methylketone group, which binds irreversibly to all of caspase types 1-14.

6. The method according to claim 2, wherein the caspase inhibitor is a peptide coupled to at least one aldehyde group.

7. The method according to claim 1, wherein the caspase inhibitor is present in a concentration of 20 μM to 100 μM in the reaction mixture.

8. The method according to claim 1, wherein the eukaryotic cell lysate contains membrane vesicles.

9. The method according to claim 8, wherein the membrane vesicles originate from a same cell line as the eukaryotic cell lysate.

10. The method according to claim 1, wherein the insect cell lysates are *Spodoptera frugiperda* cell lysates.

* * * * *

SEQUENCE LISTING

```
<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Caspase inhibitor

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: Caspase inhibitor

<400> SEQUENCE: 2

Tyr Val Ala Asp
1
```

```
<210> SEQ ID NO 3
<211> LENGTH: 4
<212> TYPE: PRT
<213> ORGANISM: Artificial Sequence
<220> FEATURE:
<223> OTHER INFORMATION: Caspase inhibitor

<400> SEQUENCE: 3

Trp Glu His Asp
1

<210> SEQ ID NO 4
<211> LENGTH: 4
<212> TYPE: PRT
<213> ORGANISM: Artificial Sequence
<220> FEATURE:
<223> OTHER INFORMATION: Caspase inhibitor

<400> SEQUENCE: 4

Ala Glu Val Asp
1

<210> SEQ ID NO 5
<211> LENGTH: 4
<212> TYPE: PRT
<213> ORGANISM: Artificial Sequence
<220> FEATURE:
<223> OTHER INFORMATION: Caspase inhibitor

<400> SEQUENCE: 5

Leu Glu Glu Asp
1

<210> SEQ ID NO 6
<211> LENGTH: 5
<212> TYPE: PRT
<213> ORGANISM: Artificial Sequence
<220> FEATURE:
<223> OTHER INFORMATION: Caspase inhibitor

<400> SEQUENCE: 6

Val Asp Val Ala Asp
1               5

<210> SEQ ID NO 7
<211> LENGTH: 4
<212> TYPE: PRT
<213> ORGANISM: Artificial Sequence
<220> FEATURE:
<223> OTHER INFORMATION: Caspase inhibitor

<400> SEQUENCE: 7

Val Glu Ile Asp
1

<210> SEQ ID NO 8
<211> LENGTH: 4
<212> TYPE: PRT
<213> ORGANISM: Artificial Sequence
<220> FEATURE:
<223> OTHER INFORMATION: Caspase inhibitor

<400> SEQUENCE: 8

Ile Glu Thr Asp
1
```

```
<210> SEQ ID NO 9
<211> LENGTH: 4
<212> TYPE: PRT
<213> ORGANISM: Artificial Sequence
<220> FEATURE:
<223> OTHER INFORMATION: Caspase inhibitor

<400> SEQUENCE: 9

Leu Glu His Asp
1

<210> SEQ ID NO 10
<211> LENGTH: 20
<212> TYPE: PRT
<213> ORGANISM: Artificial Sequence
<220> FEATURE:
<223> OTHER INFORMATION: Caspase inhibitor

<400> SEQUENCE: 10

Ala Ala Val Ala Leu Leu Pro Ala Val Leu Leu Ala Leu Leu Ala Pro
1               5                   10                  15

Asp Glu Val Asp
            20
```